United States Patent [19]

Scheller et al.

[11] 4,450,599

[45] May 29, 1984

[54] ELECTRIC TOOTHBRUSH

[75] Inventors: Hans U. Scheller; Karl A. Scheller, both of Eislingen, Fed. Rep. of Germany

[73] Assignee: Württembergische Parfümerie-Fabrik GmbH, Eislingen, Fed. Rep. of Germany

[21] Appl. No.: 371,194

[22] Filed: Apr. 23, 1982

[30] Foreign Application Priority Data

Apr. 30, 1981 [DE] Fed. Rep. of Germany ....... 3117160

[51] Int. Cl.³ ............................................. A46B 13/02
[52] U.S. Cl. ................................................. 15/22 R
[58] Field of Search ................. 15/22 R, 22 A, 22 C, 15/23, 24, 28, 29, 97, 167 R; 128/62 A

[56] References Cited

U.S. PATENT DOCUMENTS 2,319,205 5/1943 Buck ................................... 15/22 R
3,512,202 5/1970 Taylor ................................. 15/23

FOREIGN PATENT DOCUMENTS 609238 2/1979 Switzerland ...................... 15/22 R Primary Examiner—Edward L. Roberts
Attorney, Agent, or Firm—Spensley, Horn, Jubas & Lubitz

[57] ABSTRACT

An electric toothbrush having a timer for monitoring brushing time. The timer is activated when the pressure exertred on the bristles exceeds a predetermined minimum pressure to ensure proper brushing for a predetermined minimum period of time.

12 Claims, 1 Drawing Figure

U.S. Patent   May 29, 1984   4,450,599
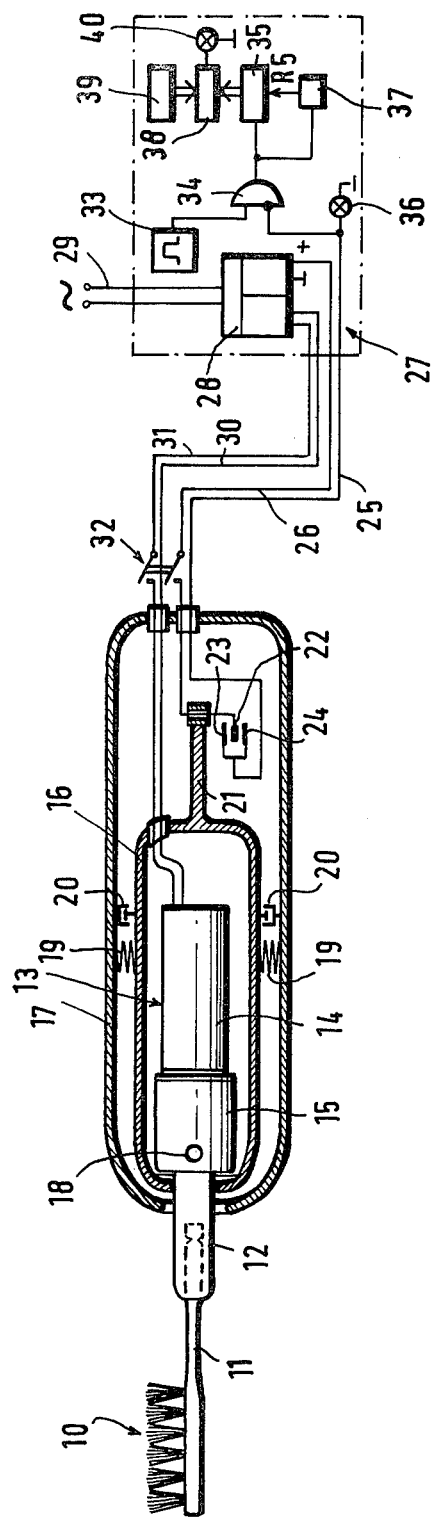

ELECTRIC TOOTHBRUSH

The invention concerns an electric toothbrush with a brush part, that is connected to an oscillatory or rotary drive, and with a timer for monitoring the brushing time.

The main cause of caries and marginal gingivitis is the formation of dental plaque. This soft adhering coating on the teeth results from the accumulation of bacteria in remnants of food, which build up preferentially at the edges of the gums. Apart from micro-organisms and their metabolic products, their main constituents are various carbohydrates, albumens and organic compounds. Effective elimination of this plaque or the reduction of its build-up rate are important objectives in oral hygiene, i.e. in the cleaning of teeth. For the purpose of completely removing plaque, it is important that brushing of the teeth should take place over a specific minimum period of time.

For the purpose of providing the user of a toothbrush with information regarding the period of use during a toothbrushing operation, it is known to fit the toothbrush with a timer, which is automatically brought into operation by the temperature of the mouth and/or the temperature of the hand (DE-OS No. 29 18 806). If the temperature threshold value has been exceeded over a specific predetermined time, a signal is produced which indicates to the user that the required minimum time for brushing of the teeth has been reached. This thermally controlled monitoring device suffers from the disadvantage that its function is greatly influenced by the ambient temperature and by other temperature factors, so that the time indications do not provide satisfactory information regarding effective treatment of the teeth. For example, an adequate brushing time is indicated even when the toothbrush is simply introduced into the mouth but is not moved. A decisive factor in the cleaning of teeth is the maintenance of a certain contact pressure, by means of which the bristles act on the teeth. In order to achieve effective mechanical operation on the teeth by the bristles and to cause the bristles also to penetrate into the gaps, this contact pressure should not be too low; nor, however, should it be too great, since this likewise reduces the effectiveness of the toothbrushing operation and it also involves a risk of injury.

The object of the present invention is to provide an electric toothbrush of the initially stated kind, by means of which monitoring of the time, during which effective treatment is carried out by the toothbrush, is achieved.

According to the invention, this object is achieved in that the timer can be switched in when the toothbrush is used and is controlled by a load-measuring device so that it operates only during that period in which the correct load is applied to the bristle part, and a signal is produced upon expiry of a pre-set minimum time.

With the toothbrush in accordance with the invention, the mechanical load applied by the bristle part or the stem is determined, and the timer registers only those periods of use in which the load lies above a certain minimum value. In this way it becomes possible for the timer to register the actual time during which the toothbrush is in effective use. Those periods during which the toothbrush is not under load or is being operated with too low a contact pressure are not shown as tooth-brushing time. An excessive load can be indicated by means of a warning signal. When the signal is produced by the timer, the user can be certain that the toothbrush has been in operation for an adequate length of time and sufficiently intensively. The toothbrush thus suits the tooth-brushing habits of the particular user. If someone habitually briefly interrupts the brushing of his teeth from time to time, then the periods of the interruptions are eliminated from the measured time, since there is not a sufficiently great contact pressure of the bristles against the teeth during these periods. The load-measuring device can be designed in any one of a large number of ways. In accordance with a further advantageous feature of the invention, the load-measuring device comprises at least one first electrical contact secured to a casing and at least one second electrical contact attached to the oscillatory drive, which is mounted within the casing so as to be resiliently movable in the transverse direction. With this arrangement, the contact pressure is determined by using the pressure-dependent movements of the oscillatory drive within the casing for actuating the electrical contacts. Other possible ways of measuring the load consist in measuring the deflection of the stem of the toothbrush or the current take-up of the motor for the oscillatory drive. These two quantities are likewise dependent upon the pressure acting on the bristle part of the toothbrush.

In order to prevent the mechanical oscillations of the oscillatory drive, that are of relatively high frequency, from acting on the timer and from producing brief loading or load-relief signals, a preferred form of the invention relates to the provision of damping means between the casing and the oscillatory drive. These damping means, on the one hand, damp down mechanical oscillations in the casing, and on the other hand, prevent the oscillatory drive from interfering with the function of the timer. Alternatively, it is possible to carry out electrical damping of the signals supplied by the load-measuring device to the timer so as to eliminate brief peaks or breaks in the signals.

The oscillatory drive is preferably mounted in the front zone of the casing by means of a spindle which extends transversely of the stem. Two first contacts can be provided in the rear zone of the casing, the second contact being movable between them. With this arrangement, measurement of time is interrupted in the case of too low a mechanical loading of the bristle part as well as in the case in which said bristle part is excessively mechanically loaded. Furthermore, it is possible, by means of signal lights or the like, to show on an indicating device whether the contact pressure is too high or too low, so that the user knows why the timer is not running.

The timer can be set in operation by pressing the operating switch of the toothbrush. Another possibility is to keep the timer continuously in a stand-by position and to switch it on when the load signal occurs. For this purpose and in accordance with a further advantageous form of the invention, a timing element is provided which returns the timer to zero after the expiry of a period of time that is less than the pre-set minimum time, and the timing element is started off again by each of the signals produced when the bristle part is under load.

An example of the construction of the toothbrush in accordance with the invention will now be described by reference to the single FIGURE forming the accompanying drawing.

In the drawing, the mechanical construction of the toothbrush and the electrical make-up of the timer are illustrated diagrammatically.

The toothbrush has a bristle part 10, which is exchangeably fitted in a holder 12 by means of a stem 11. The holder 12 is connected to an oscillatory drive 13. The oscillatory drive 13 consists of an electric motor 14, the output of which is connected to a gear 15. The output shaft of the gear 15 executes rotary oscillatory movements and it is connected to, and rotates with, the holder 12. Thus, when the motor 14 is switched on, the bristle part 10 is caused to move about the axis of the stem 11 in rotary oscillatory movements.

The oscillatory drive 13 is accommodated in an inner casing 16, which is housed in a further casing 17 which is designed to be gripped in the hand. The pivot spindle 18 is located near the front end of the casing 17 and extends transversely of the axis of the holder 12. The inner casing 16 is mounted on the spindle 18 in the casing 17 in such a way that, when pressure acts on the bristles of the bristle part 10, the inner casing 16 within the stationary casing 17 is turned about the spindle 18.

The inner casing 16 is braced against the inner wall of the casing 17 in its rear zone by means of a number of springs 19, so that in the unloaded condition of the bristle part 10, the inner casing 16 is held in a position in which it is coaxial with the casing 17. Connected in parallel with the springs 19 are damping elements 20 for eliminating the dynamic component of the oscillatory movements of the inner casing 16 about the spindle 18. In this way, only the static pressure, acting on the bristle part 10, is converted into pivotal movements of the inner casing 16 about the spindle 18.

An arm 21, which carries a contact element 22, is solidly connected to the rear end of the inner casing. The contact element 22 is insulated from the arm. In the (unloaded) rest position of the inner casing, i.e. when no pressure is applied to the bristle part 10, the contact 22 bears against a stationary contact 24. When a certain minimum pressure is exceeded, the contact 22 moves away from the contact 24, and when a certain maximum pressure is reached, the contact 22 moves into connection with a further stationary contact 23. In the present embodiment, the contacts 23 and 24 are connected to each other, and are connected to a timer 27 by way of a lead 25. The contact 22, which is movable with the inner casing 16, is likewise connected to the timer 27 by way of a lead 26. The timer 27 contains a power-pack 28 which, through a cable 29, can be connected to the supply mains and, through leads 30 and 31, supplies the current for operating the oscillatory drive 13. The power-pack 28 also supplies the lead 26 with positive potential, while also supplying current to the electrical and electronic components of the timer 27.

The leads 31 and 26 are connected by actuating the switch 32 for operating the electric toothbrush. Thus, on the one hand, the oscillatory drive 13 is brought into operation and, on the other, positive potential is applied to the contact 22.

The timer 27 contains an impulse generator 33, the output of which is connected to a counter 35 by way of an AND gate 34. The signal transmitted by the lead 25 is applied to the inverted second input of the AND gate 34. This lead 25 is also connected to an indicator light 36.

The output signal of the AND gate 34 actuates a timing element 37 with a running time of a few seconds. Upon de-energization, the timing element 37 sends a signal to the re-setting input R5 of the counter 35 so that the state of fill of the counter 35 is returned to zero.

The output of the counter 35 is connected to a comparator 38. The comparator 38 compares the state of fill of the counter 35 with the contents of an adjustable impulse-storing device 39. In the event of coincidence of the two input signals, an indicator light 40, controlled by the comparator 38, glows.

If, during operation of the toothbrush, the movable contact 22 bears against the stationary contact 23, i.e. when the pressure on the bristles is too high, the indicator light 36 is caused to show by way of the switch 32 and the contacts 22 and 23, to that there is provided an indication that the loading of the toothbrush, i.e. the bristle pressure, does not lie in the correct range. At the same time, a signal is supplied to the inverted input of the AND gate 34, so that this AND gate is blocked. The impulses from the generator 33 do not therefore reach the counter 35.

If the contact 22 is located between the contacts 23 and 24 without touching them, then an "0" signal occurs at the inverted input of the AND gate 34, so that the gate connects through and lets the impulses from the impulse generator 33 through to the counter 35. With each of these impulses, the counter 35 is again impulsed, so that the timing element 37 cannot de-energize and therefore cannot produce a re-setting signal R5 either. As soon as the state of fill of the counter 35 has reached the preset value in the impulse-storing device 39, the comparator 38 produces a coincidence signal, whereby the indicator light 40 is energized. The indicator light 40 therefore shows that the required period of operation of the toothbrush has been reached.

If the tooth-brushing process is briefly interrupted i.e. if the contact pressure against the bristle part 10 ceases, the AND gate 34 is blocked, so that it no longer lets impulses through. The timing element 37 then begins to run. When the contact pressure is continued still within the running time of the timing element 37, the AND gate 34 again switches through, and the timing element 37 is returned to the initial state. The counter 35 is not set back to zero, but instead, the amount of its current is first stored and counting is then resumed.

If the period of the interruption of the loading of the bristle part 10 or the duration of an excessive loading of the bristle part 10 exceeds the running time of the timing element 37, then this element is de-energized and returns the state of fill of the counter 35 to zero.

The described timer 27 thus registers and accumulates the actual effective periods of use and thus ensures that the indicator light 40 only shows up if the toothbrush has been effectively used over a certain period. The stoppage times and the times during which the toothbrush is not efficiently used are automatically eliminated. The lower value of the pressure that acts on the bristle part 10 and at which the contact 22 moves away from the contact 23 is 120 p, for example, and the upper pressure value, at which the contacts 22 and 24 come together, is 200 p. This range of from 120 to 200 p is that force range upon which the measurement of the time required for effective cleaning of the teeth is based.

We claim:
1. An electric toothbrush apparatus comprising:
a toothbrush having a stem and a plurality of bristles at one end of the stem;
oscillator means for imparting an oscillating motion to the toothbrush while the apparatus is operated;
timing means for timing the duration of periods of operation of the apparatus and providing an indica- tion of the total duration of accumulated periods of timed operation;

means responsive to pressure applied to the bristles of the toothbrush, for activating the timing means for the periods of operation in which the pressure applied to the toothbrush stem exceeds a predetermined minimum pressure;

comparator means responsive to the timing means, for comparing the accumulated total duration of timed operating periods with a predetermined minimum period; and signaling means responsive to the comparator means, for signaling an operator when the accumulated total duration of timed operating periods exceeds the predetermined period;

wherein the periods of operation in which the pressure applied to the toothbrush stem exceeds the predetermined minimum pressure may be timed to ensure effective utilization of the apparatus.

2. The apparatus of claim 1 further comprising deactivating means responsive to the pressure applied to the bristles of the toothbrush, for deactivating the timing means while the pressure applied during the operation of the apparatus exceeds a predetermined maximum pressure;

wherein the timed periods of operation of the apparatus exclude periods in which the pressure applied to the toothbrush bristles exceeds the predetermined maximum pressure.

3. The apparatus of claim 2 further comprising a second signaling means responsive to the deactivation means, for signaling an operator that the apparatus operation timing has been deactivated and that the pressure being applied to the toothbrush bristles is excessive.

4. The apparatus of claim 2 further comprising a second timing means responsive to the deactivating means, for resetting the timing means to an initial state when the timing means has been deactivated for a period of time exceeding a second predetermined period.

5. The apparatus of claim 1 wherein the timing means includes a pulse generator having an output, for generating a train of pulses, a counter having an input, for counting pulses, and gate means for coupling the output of the pulse generator to the input of the counter in response to the activating means wherein pulses are counted by the counter during the timed periods of operation in which the pressure applied to the toothbrush bristles during the operation of the toothbrush exceeds the predetermined minimum pressure.

6. The apparatus of claim 1 further comprising a housing wherein the toothbrush is pivotably coupled to the housing, and the activating means includes a switch having a stationary contact coupled to the housing and a movable contact coupled to the toothbrush stem wherein the switch is actuated in response to the application of pressure to the toothbrush bristles in excess of the predetermined minimum.

7. The apparatus of claim 1 further comprising a housing wherein the toothbrush stem is pivotably coupled to the housing, and the activating means and deactivating means include a switch having first and second stationary contacts coupled to the housing and a movable contact coupled to the toothbrush stem, the movable contact being movable between the first and second stationary contacts wherein the movable contact rests against the first stationary contact until the pressure applied to the toothbrush stem exceeds the predetermined minimum pressure, the movable contact engages the second stationary contact when the pressure applied to the toothbrush stem exceeds the predetermined maximum and the movable contact is disengaged from both stationary contacts when the pressure applied to the toothbrush stem is intermediate the predetermined minimum and maximum pressures.

8. The apparatus of claim 7 wherein the oscillator means further includes means for holding the toothbrush stem, the apparatus further comprising a spindle by which the oscillatory means is pivotably mounted within the housing.

9. The apparatus of claim 8 further comprising damping means disposed between the housing and the oscillator means, for damping the pivotal motion of the oscillator means.

10. An electric toothbrush apparatus comprising:
a toothbrush having a stem and a plurality of bristles at one end of the stem;
oscillator means for holding the toothbrush stem at the other end of the stem and imparting an oscillating motion to the toothbrush;
a housing for the oscillator means;
a spindle for pivotably mounting the oscillator means within the housing;
a switch having first and second stationary contacts coupled to the housing and a movable contact coupled to the oscillator means and carried between the first and second stationary contacts wherein the movable contact engages the first stationary contact while the pressure applied to the toothbrush bristles is below a predetermined minimum pressure and the movable contact engages the second stationary contact when the pressure applied to the toothbrush bristles exceeds a predetermined maximum pressure thereby defining closed positions of the switch, the switch also having an open position in which the movable contact is disengaged from both of the stationary contacts as a result of a pressure intermediate the predetermined maximum and minimum pressures being applied to the toothbrush bristles;
pulse generator means for generating a sequential train of timing pulses;
a counter for counting pulses to time the duration of operation;
gate means for gating the pulses to the counter while the switch is in the open position and for blocking the train of pulses from the counter when the switch is in the closed position;
storage means for storing signals representative of a predetermined number of pulses which represent a predetermined time interval;
comparator means for comparing the number of pulses counted by the counter with the predetermined number stored in the storage means;
first indicator means responsive to the comparator means for providing an indication to an operator that the duration of operation in which the switch was open exceeds the predetermined period;
second indicator means responsive to the closed position of the switch for indicating that the pressure applied to the toothbrush bristles is below the predetermined minimum or in excess of the predetermined maximum; and
reset means responsive to the gate means for resetting the counter when the absence of pulses from the pulse generator exceeds a second predetermined period.

11. A toothbrush apparatus comprising:
a toothbrush stem which has bristles on one end;
timer means for timing, when activated, the operation of the toothbrush; and
means responsive to pressure applied to the toothbrush bristles, for activating the timer means when the pressure applied to the toothbrush bristles exceeds a predetermined minimum pressure.

12. In an electric toothbrush apparatus which includes a toothbrush having a stem and a plurality of bristles at one end of the stem, and oscillator means for imparting an oscillating motion to the toothbrush while the apparatus is operated, the improvement comprising:
timer means for timing, when activated, the operation of the apparatus; and
means responsive to pressure applied to the bristles of the toothbrush, for activating the timer means when the pressure applied to the toothbrush bristles exceeds a predetermined minimum pressure.

* * * * *